US00PP23857P2

(12) United States Plant Patent
Klemm et al.

(10) Patent No.: US PP23,857 P2
(45) Date of Patent: Aug. 27, 2013

(54) **NEW GUINEA *IMPATIENS* PLANT NAMED 'KLENI11124'**

(50) Latin Name: *Impatiens hawkeri*
Varietal Denomination: KLENI11124

(75) Inventors: Nils Klemm, Stuttgart (DE); Katinka Wilde, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 21 days.

(21) Appl. No.: 13/506,034

(22) Filed: Mar. 22, 2012

(51) Int. Cl.
*A01H 5/00* (2006.01)

(52) U.S. Cl.
USPC ..... Plt./318.1; Plt./318.6

(58) Field of Classification Search
USPC ..... Plt./318.1, 318.6, 318.7
See application file for complete search history.

*Primary Examiner* — Kent L Bell
(74) *Attorney, Agent, or Firm* — Jondle Plant Sciences Division of Swanson & Bratschun, L.L.C.

(57) ABSTRACT

A new New Guinea *Impatiens* plant named 'KLENI11124', particularly distinguished by its early flowering and red-purple to red flowers, is described.

1 Drawing Sheet

Genus and species: *Impatiens hawkeri.*
Variety denomination: 'KLENI11124'.

BACKGROUND OF THE NEW PLANT

The present invention comprises a new and distinct variety of New Guinea *Impatiens*, botanically known as *Impatiens hawkeri*, and hereinafter referred to by the variety name 'KLENI11124'. The new variety originated from a controlled hybridization between female New Guinea *Impatiens* plant 'A 923' (unpatented) and male New Guinea *Impatiens* plant '2006 0042' (unpatented) from July to October 2007 in Nairobi, Kenya.

The new variety was first propagated via vegetative cuttings in the summer of 2008 in Stuttgart, Germany and has been asexually reproduced repeatedly by vegetative cuttings in Stuttgart, Germany for more than 40 generations. 'KLENI11124' has been found to retain its distinctive characteristics through successive asexual propagations.

Plant Breeder's Rights for this variety were applied for in Switzerland on Jul. 4, 2011 and in the European Union on Jul. 8, 2011. 'KLENI11124' has not been made publicly available more than one year prior to the filing of this application.

SUMMARY OF THE INVENTION

The following are the most outstanding and distinguishing characteristics of this new variety when grown under normal horticultural practices in a glass greenhouse in Stuttgart, Germany 1. Early flowering; and
2. Red-purple to red flowers.

DESCRIPTION OF PHOTOGRAPH

This New Guinea *Impatiens* plant is illustrated by the accompanying photograph which shows the overall plant habit including blooms, buds, and foliage of the plant. The colors shown are as true as can be reasonably obtained by conventional photographic procedures. The photograph is of a plant 3 months old, grown from rooted cuttings in a 10.5 centimeter pot in a glass-covered greenhouse in the winter of 2011-2012 in Stuttgart, Germany, under conditions which approximate those generally used in normal horticultural practice.

DESCRIPTION OF THE NEW VARIETY

The following detailed descriptions set forth the distinctive characteristics of 'KLENI11124'. The data which defines these characteristics were collected from asexual reproductions carried out in Stuttgart, Germany. The plant history was taken in the winter of 2011-2012 on 18 week old plants which were planted as rooted cuttings in 10.5 cm pots, and then grown in a glass-covered greenhouse. Color readings were taken under artificial light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Balsaminaceae.
- *Botanical name.*—*Impatiens hawkeri.*
- *Designation.*—'KLENI11124'.
- *Common name.*—New Guinea *Impatiens.*

Parentage:
- *Female parent.*—New Guinea *Impatiens* plant, 'A 923' (unpatented).
- *Male parent.*—New Guinea *Impatiens* plant, '2006 0042' (unpatented).

Growth:
- *Growth and branching habit.*—Compact; round.
- *Height.*—15.0 cm.
- *Width.*—25.0 cm.
- *Propagation.*—Vegetative cuttings.
- *Time from rooted cutting to flowering plant.*—43 to 50 days in the spring.
- *Time to initiate and develop roots.*—20 days.

Branches:
*Average number.*—11.
*Length of branches.*—10.0 cm.
*Internode length.*—2.5 cm.
*Diameter of branches.*—0.9 cm.
*Stem color.*—RHS 183A.

Leaves:
*Arrangement.*—Base of the plant: Opposite. Middle and upper section of the plant: Whorled.
*Length.*—10.0 cm.
*Width.*—3.7 cm.
*Shape.*—Oblong to lanceolate.
*Apex.*—Acuminate.
*Base.*—Acuminate.
*Margin.*—Shallow serrate.
*Color* (*both mature and immature leaves*).—Upper surface: RHS N189A. Lower surface: RHS N186C.
*Texture* (*both surfaces*).—Leathery, glossy.
*Venation pattern.*—Feather-like.
*Venation color.*—Upper surface: RHS 186A. Lower surface: RHS 187C.
*Variegation.*—Absent.
*Petioles.*—Length: 3.0 cm. Diameter: 0.3 cm. Color: Upper surface: RHS 182D. Lower surface: RHS 182A. Texture (both surfaces): Smooth.

Peduncle:
*Color.*—RHS 151A.
*Length.*—2.8 cm.
*Diameter.*—0.2 cm.
*Texture.*—Smooth.

Flower buds:
*Shape.*—Ovoid, completely closed.
*Length.*—2.0 cm.
*Diameter.*—1.2 cm.
*Color.*—RHS 42A.
*Texture.*—Smooth.

Inflorescence:
*Blooming habit.*—Continuous.
*Inflorescence type.*—Single flower arranged in clusters arising from the leaf axil; flower positioned above the foliage; flowers face upward and outward.
*Number of flowers per node.*—1 to 4 plus 2 buds.
*Flowering season.*—April to Fall in Europe.
*Lastingness of individual blooms on the plant.*—14 to 21 days.
*Fragrance.*—Absent.

Corolla:
*Form.*—Single.
*Number of petals.*—5.
*Shape.*—Round to oval.
*Length.*—6.8 cm.
*Width.*—7.0 cm.
*Depth.*—0.4 cm.

Petals:
*Shape.*—Cordate.
*Apex.*—Petals are medium incised in the middle.
*Base.*—Round to acute.
*Margin.*—Entire.
*Size.*—Upper petals: Length: 3.0 cm. Width: 4.5 cm. Lateral petals: Length: 3.4 cm. Width: 4.1 cm. Lower petals: Length: 3.2 cm. Width: 3.6 cm.
*Color.*—Upper surface: RHS N66D and RHS 41A. Lower surface: RHS 33A. Eye Zone: RHS N66A.
*Texture* (*both surfaces*).—Satiny, smooth.

Spur:
*Shape.*—Oblong to acute.
*Color.*—RHS 47A.
*Length.*—4.5 cm.
*Diameter.*—Proximal 0.1 cm, distal 0.2 cm.

Sepals:
*Quantity per flower.*—5.
*Arrangement.*—Whorled, overlapping.
*Lateral sepals.*—Shape: Acuminate, entire. Length: 4.5 cm. Width: 2.8 cm.
*Lower sepals.*—Shape: Acuminate, entire. Length: 3.0 cm. Width: 3.5 cm.
*Surface texture* (*both surfaces*).—Smooth.
*Color.*—Upper surface: RHS 50A in a flamed pattern, RHS 68B in the center. Lower surface: RHS 68B.

Reproductive organs:
*Stamens.*—Number and arrangement: 5 stamens are fused, forming a cap over the ovary. Anther color: RHS 159C. Anther length: 0.4 cm. Pollen color: RHS 158D. Pollen amount: Medium.
*Pistils.*—Style and stigma: Hair-like. Arrangement: 5 styles and stigmas fused together; arranged in a circle on top of ovary. Style color: RHS 59A. Style length: 0.7 cm. Stigma color: RHS 59B. Ovary: Shape: Ovate. Length: 0.6 cm. Color: RHS 137A.

Fruit and seed set: Seed production has not been observed.

Disease and insect resistance: Plants have medium tolerance to red spider mite.

COMPARISON WITH PARENTAL AND COMMERCIAL VARIETIES

'KLENI11124' differs from the female parent 'A 923' (unpatented) by having red-purple to red flowers, while 'A 923' has purple and white flowers.

'KLENI11124' differs from the male parent '2006 0042' (unpatented), by having red-purple to red flowers, while '2006 0042' has red flowers.

'KLENI11124' differs from the commercial New Guinea *Impatiens* variety 'KLEI04073' (European Plant Breeder's Rights no. 18967) by having flowers colored RHS N66D and RHS 41A, while 'KLEI04073' has flowers colored RHS 57A.

We claim:

1. A new and distinct variety of New Guinea *Impatiens* plant named 'KLENI11124' as shown and described herein.

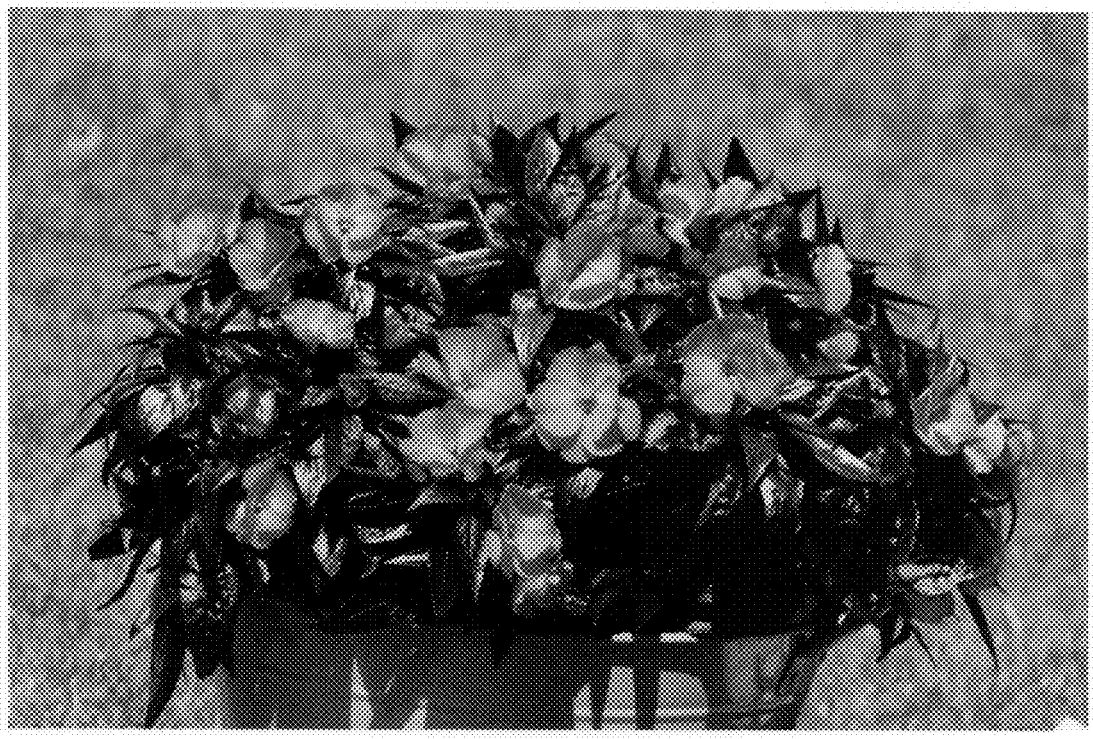

* * * * *